United States Patent [19]
Slettenmark

[11] Patent Number: 5,318,521
[45] Date of Patent: Jun. 7, 1994

[54] DOSING DEVICE FOR THE CONTROLLED DELIVERY OF A LIQUID

[75] Inventor: Bruno Slettenmark, Jaerfaella, Sweden

[73] Assignee: Siemens Aktiengesellschaft, Munich, Fed. Rep. of Germany

[21] Appl. No.: 54,146

[22] Filed: Apr. 30, 1993

[30] Foreign Application Priority Data

May 12, 1992 [EP] European Pat. Off. ......... 92107994.3
Oct. 26, 1992 [EP] European Pat. Off. ......... 92118257.2

[51] Int. Cl.⁵ .............................................. A61M 5/20
[52] U.S. Cl. ......................................... 604/67; 604/152
[58] Field of Search .................................. 604/65–67, 604/151, 152; 128/DIG. 12, DIG. 13; 417/415, 63

[56] References Cited
U.S. PATENT DOCUMENTS

| | | | |
|---|---|---|---|
| 4,346,705 | 8/1982 | Pekkarinen et al. | 604/152 |
| 4,360,019 | 11/1982 | Portner et al. | |
| 4,838,860 | 6/1989 | Groshong et al. | 604/152 |
| 4,985,015 | 1/1991 | Obermann et al. | 604/67 |

FOREIGN PATENT DOCUMENTS 0110117 6/1984 European Pat. Off. .
0183351 6/1986 European Pat. Off. .

*Primary Examiner*—John D. Yasko
*Assistant Examiner*—Anthony Gutowski
*Attorney, Agent, or Firm*—Hill, Steadman & Simpson

[57] ABSTRACT

In a dosing device of the type suitable for human implantation for delivering a liquid medicament, a piston of a pump is accelerated against a detent by energization of an electromagnetic actuation system, with the electromagnetic actuation system being controlled so that it is de-energized slightly before the piston reaches the detent, with the inertia of the piston carrying the piston against the detent to complete the piston stroke. By shortening the amount of time during which the electromagnetic actuation system is energized, energy is saved. Control of the electromagnetic actuation system is undertaken by identifying a nominal stroke time for the piston by detecting the impact of the piston against the detent, and calculating an on time for the electromagnetic actuation system which is so short that the impact of the piston against the detent can still be just barely detected.

22 Claims, 3 Drawing Sheets

DOSING DEVICE FOR THE CONTROLLED DELIVERY OF A LIQUID

BACKGROUND OF THE INVENTION

1. Field of the Invention

The present invention is directed to a dosing device for the controlled deliver of a liquid from a reservoir, and in particular to such a device which is suitable for human implantation for delivering liquid medication.

2. Description of the Prior Art

A dosing device is disclosed in European Application 0 317 705 for injecting insulin from a reservoir into the body of a patient. This known device has a piston pump having a piston which can be moved through a stroke from a quiescent position to a position against a detent of a cylindrical housing surrounding the piston by means of an electromagnetic actuation system which can be switched on and off (energized and deenergized). A pump rate generator generates an "on signal" for energizing the electromagnetic actuation system for a time during each piston stroke. A detector generates an output signal when the piston strikes against the detent, the output signal being used in an evaluation means for generating an "off signal" for de-energizing the electromagnetic actuation system.

This known device is a battery operated implant, and in order to be able to monitor the course of the pump function, a detector is provided which indirectly acquires a signal corresponding to the motion course (such as an acceleration curve) of the piston, and detects when the piston strikes against the detent. The output signal generated by this detector is used for de-energizing the electromagnetic actuation system, so that it is assured that the pump is switched off at the end of each pump stroke, and further energy is thus not drawn from the battery.

SUMMARY OF THE INVENTION

It is an object of the present invention to provide a dosing device for the controlled delivery of a liquid wherein the energy consumption of the piston pump is even further reduced, in order to lengthen the useful implantation life of the device and/or to make the device smaller in size by permitting the use of a smaller battery.

It is-a further object of the present invention to reduce the effects of unnecessarily high mechanical vibrations, caused by the impact of the piston against the detent, on the liquid to be pumped, the pump mechanism itself, and the associated electronics.

It is a further object of the present invention to provide such a device wherein the noise due to operation thereof is reduced.

Another object of the present invention is to provide such a device having a further signal available for use in diagnosing the condition of the device.

The above objects are achieved in a dosing device constructed in accordance with the principles of the present invention, of the type described above having an electromagnetically actuated piston pump, and including evaluation means for generating the on and off signals for the actuation system, wherein the off signal is generated after the expiration of an "on-time" duration following the appearance of the on signal, the length of said on-time duration being dimensioned shorter than the actual time required for the complete stroke movement of the piston from the quiescent position to a position against the detent given fault-free operation of the dosing device. The on-time duration is lengthened when the number of detected strikings of the piston against the detent falls below a predetermined value for a given number of piston strokes.

In the simplest embodiment, the on-time duration is dimensioned sufficiently long to accelerate the piston against the detent, given fault-free operation of the dosing device, and the evaluation means uses the output signal of the detector which detects impact of the piston against the detent as the off signal for calculating and adjustment to the on-time duration. Alternatively, the on-time duration can be lengthened by a selected amount each time a striking of the piston against the detent, after actuation of the piston, is failed to be detected, so that a value for the on-time duration which is sufficient for accelerating the piston against the detent is automatically found very quickly. The on-time duration can be reset to the original, nominal value periodically, either automatically or manually by the patient or by a physician, since deviations therefrom may be of a temporary nature.

In the first instance, the time required for the piston to complete a stroke from the quiescent position to striking of the detent is measured, and in the next stroke the electromagnetic actuation system is de-energized slightly before the accelerated piston strikes the detent. Due to the kinetic energy of the piston and of the liquid in front of and behind the piston, as well as due to the energy of the magnetic field built up in the electromagnetic actuation system, the piston continues to be driven to the detent, even after the electromagnetic excitation has been removed by turning off the electromagnetic actuation system. The energy consumption for driving the piston is thus considerably reduced.

A further advantage of the dosing device disclosed herein is that the piston will strike against the detent with a lower speed than in known dosing devices, due to the premature de-energization of the electromagnetic actuation system, and the maximum speed reached by the piston during its stroke is also lower than in known devices. Mechanical stressing of the liquid to be conveyed is thereby reduced, this being of particular significance given insulin and other liquid medications because, among other things, the proteins contained in such medication are extremely sensitive to mechanical stresses. The liquid is compressed to a lesser degree than in known devices between the impact faces of the piston and of the detent due to the reduced impact speed of the piston against the detent. Moreover, mechanical stressing of the pump itself, vibrations in electronic circuits, and the generation of noise, which can be irritating to the patient, are also reduced. Due to the reduced maximum speed of the piston, turbulances in the liquid to be conveyed are avoided, and shearing forces within the liquid are reduced. By maintaining the acceleration of the piston below a selected critical value, the pressure in the liquid is also prevented from falling below its vapor pressure behind the piston, i.e., at the inlet side thereof, and thereby avoiding the appearance of cavitation phenomena. Such cavitation phenomena result in a high mechanical stressing of the liquid, and can also lead to damage of the device, for example erosion of the piston pump, as well as leading to mis-detections by the impact detector due to the mechanical pressure waves caused by such cavitation. Moreover, insulin solutions are extremely sensitive to hydrophobic interaction, i.e., at the boundary surface between the liquid phase and the vapor phase, and the preventing of cavitation phenomena is also important for this reason.

Although the piston pump in the device disclosed herein is operated with minimum energy, reliable operation of the pump is always ensured, because the on-time duration for the electromagnetic excitation is lengthened when striking of the piston against the detent is not detected. The lengthening can be automatically cancelled after the expiration of a prescribed time span, or can be manually cancelled by the patient or a physician.

In a further embodiment of the dosing device of the invention, in order to calculate the shortest possible on-time duration for a complete pump stroke, the evaluation means shortens the on-time duration step-by-step in successive pump strokes proceeding from a value at which an output signal of the detector is obtained until an output signal from the detector is absent. Subsequently, the on-time duration is lengthened by a prescribed amount, this procedure being repeated with uniform intervals in order to dynamically match the on-time duration to an altered energy consumption of the pump. As a result, the on-time duration, during which the electromagnetic actuation system is energized, is automatically adapted to altered operating conditions of the piston pump. Such altered conditions can include, for example, changes in the pump rate, changes in the friction between the piston and cylinder housing, wear and modifications of movable parts, obstacles to the liquid flow in front or behind the piston, for example due to blockage, and the occurrence of air or gas in the liquid or other modifications of the liquid. Identification of the shortest possible on-time duration for an effective pump action can be constantly repeated, or can be repeated at defined time intervals.

In order to assure that a complete pump action is still present at that time at which the output signal of the detector is absent in the calculation of the shortest time interval for an effective pump action, in a further embodiment of the invention, the detector means detects the striking of the piston against the detent with a prescribed sensitivity threshold. The step width by which the shortening of the on-time duration ensues is then dimensioned to a value which is shorter than the difference between the on-time duration with which the piston just barely reaches the detent, and the time duration with which striking of the piston against the detent upwardly exceeds the sensitivity threshold.

For monitoring the functionability of the piston pump, in a further embodiment of the invention, an error detector is provided which is connected to the evaluation means, the error-detector generating an error alarm signal when the length of the on-time duration which has been set upwardly exceeds a prescribed maximum value, or downwardly exceeds a prescribed minimum value.

In another embodiment of the dosing device of the invention, a data memory into which the current value for the on-time duration is continuously entered, or is entered given the absence of an output signal of the impact detector, is connected to the evaluation means. Together with the value for the on-time duration, the associated current value of the pump rate, and the points in time of the beginning of the motion of the piston and the striking of the piston against the detent are also stored. As a consequence of the inductance in the electrical circuit for the electromagnetic actuation, the current thereof reaches such a strength that the static (inertial) forces are overcome, and the acceleration of the piston begins only after a slight delay. The isolated absence of an output signal of the impact detector for individual pump strokes need not necessarily denote a malfunction in the operation of the piston pump. Only when a detection of the striking of the piston against the detent is absent on a frequent basis is an error message generated. In such a case, the cause of the malfunction can be subsequently identified by evaluating the events wherein a striking of the piston against the detent were not detected, those events being stored in the memory with a chronological indication of when they occurred. The identification of the cause of the malfunction can then take place either automatically in the evaluation means or by a person such as a physician who reads the data out of the memory, such as by means of a telemetry system. A possibly impending (future) malfunction of the pump operation can then be identified in advance, and corrective measures can be taken.

DESCRIPTION OF THE PREFERRED EMBODIMENTS

Figure 1:
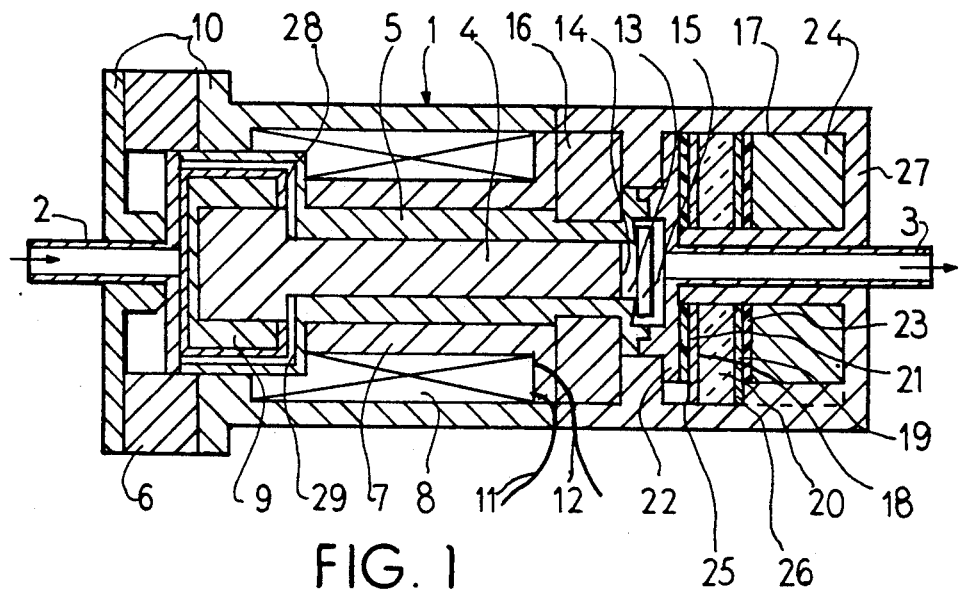
FIG. 1 is a cross-sectional view of the mechanical portion of a dosing device constructed in accordance with the principles of the present invention, in the form of an implantable medication delivery device.

In the exemplary embodiment of a piston pump I for use in a dosing device constructed in accordance with the principles of the present invention, the piston pump 1 has an inlet channel 2 and an outlet channel 3 for a liquid to be conveyed. The piston pump 1 can be a component, for example, of an implantable medication dosing device operated by a battery implanted as a part of the device. If so used, the inlet channel 2 is connected to a reservoir (not shown) for the liquid medication, for example insulin, and the outlet channel 3 will be connected to a catheter arrangement (not shown) for delivering the medication to a selected location in the body of the patient in whom the device is implanted.

The piston pump I has a piston 4 which is contained in a cylinder housing 5. The drive of the piston 4 ensues by means of an electromagnetic actuation system formed by a permanent magnet 6 arranged in the region of the inlet channel 2, a stator 7 seated on the cylinder housing 5 and having a stator winding 8, and an encapsulated armature 9 rigidly connected to the piston 4, and disposed substantially between the permanent magnet 6 and the stator 7. The pole pieces of the permanent magnet 6 and of the stator 7 are respectively referenced 10. The stator winding 8 is connected via terminal lines 11 and 12 to a control circuit, shown in greater detail in FIG. 2. The displacement region 13 (stroke length) of the piston 4 is limited by the end face 14 of the piston 4 facing toward the outlet channel 3, by the cylinder housing 5, and by a valve 15 which is seated in a position which seals the displacement region 13 with the force of a magnet 16.

The piston 4 is maintained in the quiescent position illustrated in FIG. 1 by the permanent magnet 6. Upon excitation of the stator winding 8, the piston 4 is accelerated out of its quiescent position in the direction toward the valve 15, and thereby presses the liquid situated in the displacement region 13 through the valve 15, which opens against the restoring force of the magnet 16, and into the outlet channel 3. At the same time, liquid from the reservoir is caused by suction to flow in through the channel 2 at the back side of the piston 4. This liquid is drawn by suction through the gap between the piston 4 and the portion of the cylinder housing 5 surrounding the piston 4 into the displacement region 13, when the piston 4 is moved back to its quiescent position by the force of the permanent magnet 6, upon disconnection of the excitation of the stator winding 8.

A detector in the form of a noise sensor 17 is disposed in the region of the outlet channel 3, concentrically relative to the channel 3. The noise sensor 17 is formed by piezoceramic annular disc 20 provided with metal layers 18 and 19 at both sides. The annular disc 20 is secured at one side to a flange 22 of the piston pump I via an insulating layer 21, and is connected at an opposite side to a coupling compound 24 via a further insulating layer 23. The metal layers 18 and 19 serve as sensor electrodes, and are connected to terminal lines 25 and 26 which are conducted to the exterior of the pump 1. The noise sensor 17 is contained in a housing 27 which is fixed to the piston pump 1.

The armature 9, rigidly connected to the piston 4, has an annular surface 28 facing in the direction toward the outlet channel 3. A surface of the cylinder housing 5 in the form of a detent 29 is disposed opposite the annular surface 28 with the annular surface 28, in the quiescent position shown in FIG. 1, being spaced from the detent 29. For each complete pump stroke, the annular surface 28 of the armature 9 of the piston 4 strikes against the detent 29, causing the generation of an impact noise which is distinct from the general pump noise. This impact noise is transmitted to the noise sensor 17 via the cylinder housing 5 and the flange 22, and is therein converted into an electrical output signal, which can be tapped across the terminal lines 25 and 26.

Figure 2:
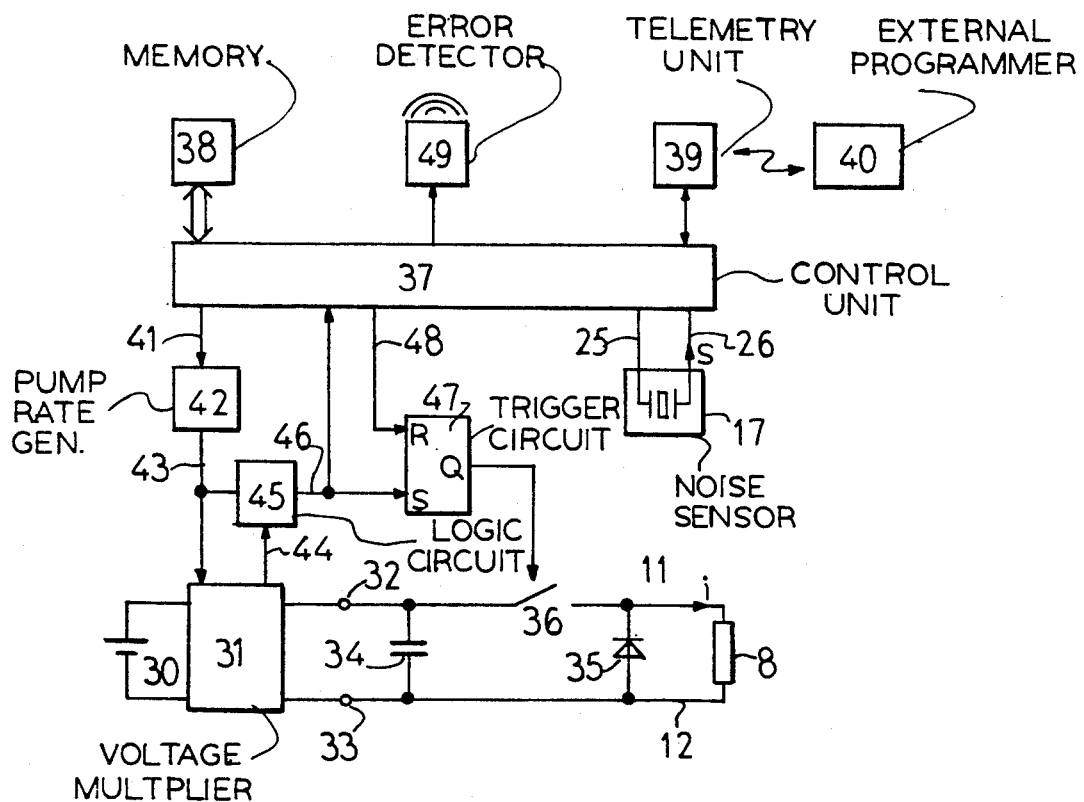
FIG. 2 is a schematic block diagram of a control and monitoring circuit constructed in accordance with the principles of the present invention for the device shown in FIG. 1.

A schematic circuit diagram of a control and monitoring circuit for the piston pump I is shown in FIG. 2. The circuit includes a voltage multiplier 31, having output terminals 32 and 33 connected to a charging capacitor 34 and having supply terminals connected to a battery 30. The stator winding 8 of the piston pump 1, together with a free-running diode 35 connected between its terminal lines 11 and 12 are connected in parallel with the charging capacitor 34 via a controllable switch 36. The control of the excitation of the stator winding 8 ensues with a higher-ranking control unit 37, which is connected to a data memory 38. A telemetry unit 39 is connected to the memory 38 for two-way communication with an external programming device 40. a number of different conveying (pumping) rates can be stored in the memory 38, which can be called automatically according to a prescribed program sequence, or can be called upon actuation of the programming device 40. The selected rate is transmitted to a pump rate generator 42 via a control line 41.

The pump rate generator 42 generates a sequence of individual pulses at an output line 43, each individual pulse defining an individual pump stroke of the piston pump 1. The pulse repetition rate is proportional to the conveying rate currently in force. The output line 43 of the pump rate generator 42 is connected to an activation input of the voltage multiplier 31. The voltage multiplier 31 is switched on (enabled) at each individual pulse, and generates a signal at a monitoring output 44 as soon as the charging capacitor 34 is charged to a prescribed, minimum voltage. Upon the appearance of the signal at the monitoring output 44, and the prior appearance of an individual pulse on the control line 43, a logic circuit 45 generates an output signal on an output signal line 46 which is supplied both to the control unit 37 and to the setting input S of a bistable trigger circuit 47.

The bistable trigger circuit 47 generates a signal at its output Q, which is supplied to the controllable switch 36 as a turn-on (beginning energization) signal. Simultaneously, the counting of a time duration is started in the control unit 37, the bistable trigger circuit 47 being reset at its reset input R via a control line 48 after the expiration of this time duration, and thereby generating a turn-off (end energization) signal at its output Q for the controllable switch 36.

Both terminal lines 25 and 26 of the noise sensor 17 are connected to the control unit 37. The output signal of the noise sensor 17 is analyzed in an evaluation means (not separately shown) which is an integral component of the control unit 37. An error detector 49 is connected to the control unit 37, which generates an error message such as, in the illustrated embodiment, an acoustic signal. It is also possible that the error message may be in the form of an electrical stimulation pulse (tickle) to the patient, or a talemetric transmission of the error message to the programming device 40.

Figure 3:
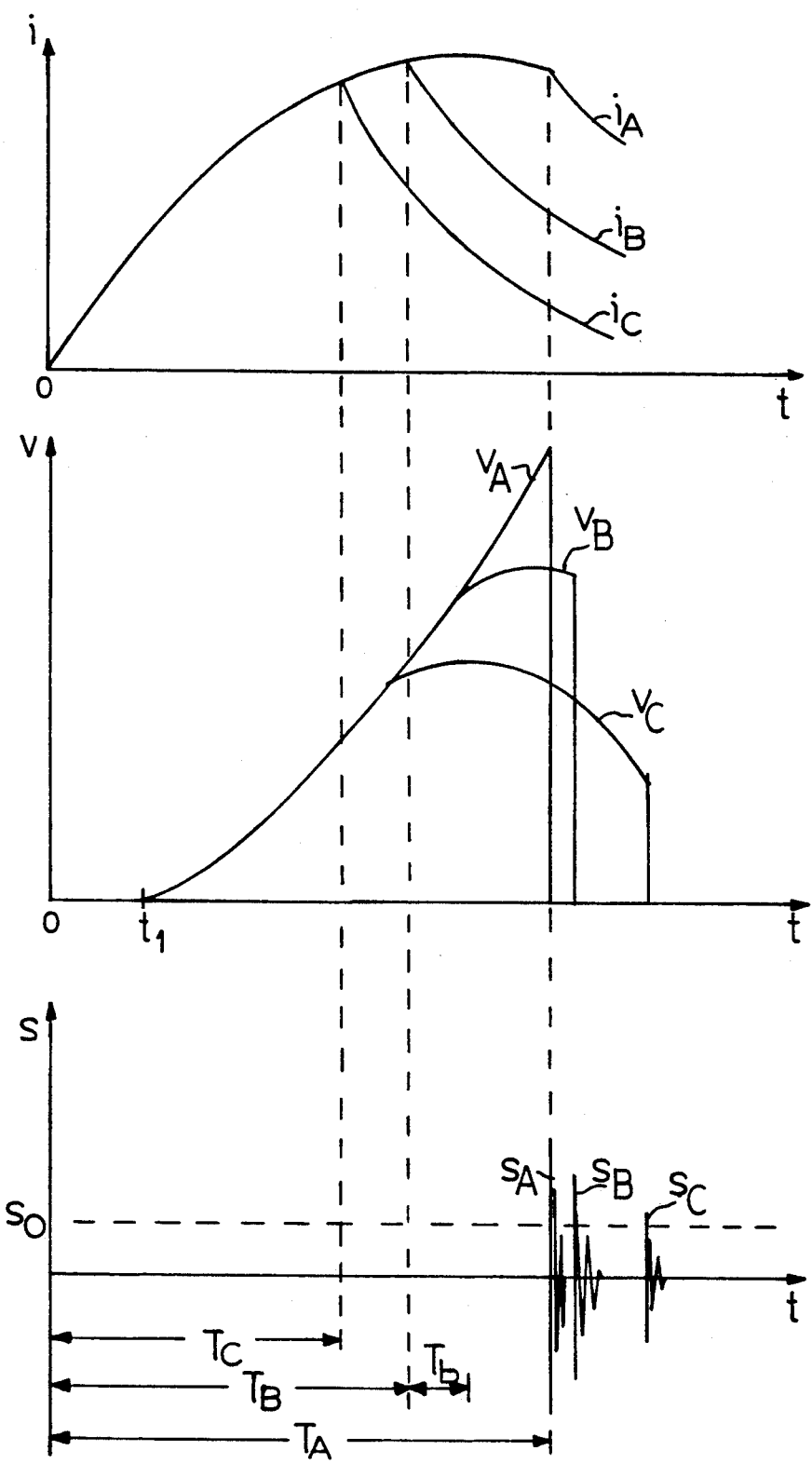
FIG. 3 shows respective curves for the excitation current for the piston pump, the speed of the piston, and the output signal of a detector for the device shown in FIG. 1.

Three curves are shown in FIG. 3 which, from top to bottom, illustrate the current i through the stator winding 8, the velocity v of the piston 4, and the output signal s of the noise sensor 17 for three different on-time durations $T_A$, $T_B$ and $T_C$, during which the controllable switch 36 is closed. The curves for the current i, the piston velocity v and the output signal s allocated to the different time intervals $T_A$, $T_B$ and $T_C$ are correspondingly indexed with subscripts A, B and C.

A pump stroke is started at time t=0, by closing the switch 36 as a result of a turn-on signal at the output Q of the trigger circuit 47. The charging capacitor 34 is discharged across the stator winding 8, in which a current i flows in the form of an attenuated sinusoidal oscillation. When the stator magnetic field generated by the current i in the stator winding 8 exceeds the retaining force of the permanent magnet 6, the stator friction of the piston 4 in the cylinder housing 5 (occurring at $t=t_1$ in FIG. 3), the piston 4 is accelerated in a direction toward the valve 15, whereby the piston velocity v progressively increases.

In the case denoted by the subscripts A, which corresponds to the pump control disclosed by the aforementioned European Application 0 317 705, the switch 36 remains closed until the piston 4 strikes the detent 29. The typical output signal $S_A$ of the noise sensor 17 thereby arising exceeds the sensitivity threshold $s_o$ thereof for the detection of the impact of the piston 4 against the detent 29, and is used for triggering a turn-off signal for the switch 36, which ends the on-time duration $T_A$. As shown in FIG. 3, the piston velocity $v_A$ reaches its maximally possible value at the end of the on-time duration $T_A$, so that the piston 4 strikes the detent 29 with the highest possible impact energy. During continuous operation of the piston pump 1, this high impact energy can lead to mechanical damage to the piston pump 1, and to an undesirably high mechanical stressing of the liquid to be conveyed. As can be seen from the curve $i_A$ of the current, moreover, the energy consumption is comparatively high. Additionally, the impact noise can be burdensome to the patient and to those around the patient.

In a first embodiment of the invention, a fixed value $T_B$ is provided for the on-time duration, this being calculated, for example, on the basis of experimental trials and being dimensioned so short that the excitation of the stator winding 8 is disconnected before the piston 4 strikes the detent 29 but being sufficiently long to obtain a sufficiently high impact energy of the piston 4 given malfunction-free operation of the piston pump 1. This means that the output signal $s_B$ of the noise sensor 17 is sure to exceed the sensitivity threshold $s_o$. At the beginning of the pump stroke, therefore, a turn-on signal for the switch 36 is generated by setting the trigger circuit 47. After the expiration of the predetermined on-time duration $T_B$, the trigger circuit 47 is reset and the switch 36 is opened by a turn-off signal at the output Q of the trigger circuit 47. The magnetic energy stored in the stator winding 8 at the time of turn-off results in the current $i_B$ continuing to flow through the stator winding 8 and the free-running diode 35, with the current $i_B$ exponentially decaying due to the internal resistance of the stator winding 8.

Due to the kinetic energy of the piston 4 and of the liquid in front of and behind the piston 4, as well as due to the magnetic energy stored in the stator winding 8 at the turn-off time, the piston 4 continues to be driven toward the detent 29, and upon impact with the detent 29 generates the output signal $s_B$ in the noise sensor 17. As can be seen in FIG. 3, both the current consumption and the maximum piston velocity, as well as the impact energy of the piston 4, are lower than in the known drive mode referred to by subscripts A set forth above. It should be noted that the impact energy is a quadratic function of the impact velocity. The piston acceleration also becomes lower in comparison to the aforementioned known drive mode, which is advantageous in order to prevent cavitation. As a result, the mechanical stressing of both the piston pump 1 and the liquid to be pumped is lower.

If, due to disturbances of any type, the number of impacts of the piston 4 detected by the noise sensor 17 for a given number of past strokes falls below a prescribed value, this is registered by the control unit 37. The control unit 37 thereupon lengthens the on-time duration, and after the expiration of the on-time duration the bistable trigger circuit 47 is reset in the subsequent pump strokes. This occurs either by the time interval $T_B$ being lengthened by a prescribed amount $T_b$, or by not generating the turn-off signal for the switch 36 until the appearance of an output signal s from the noise sensor 17 indicating the detection of the impact of the piston 4 against the detent 29.

Simultaneously, the occurrence of the malfunction event together with other pump parameters such as, for example, the current pump rate, the time interval $T_A$ and the time $t_1$ are stored in the memory 38, so that this information can recalled by a physician using the programming device 40 for error evaluation. Moreover, the patient is informed of the occurrence of a malfunction by the error detector 49, by an acoustic signal or by a stimulation current pulse. Alternatively, the patient can be informed of the error message upon the next interaction with the telemetry means, or upon his or her next visit to the physician. The lengthened time interval can be manually reset to the earlier value $T_B$ via the programming device 40. It is also possible, however, that resetting to the earlier value $T_B$ can automatically ensue upon the expiration of a programmed time within the control unit 37.

Figure 4:
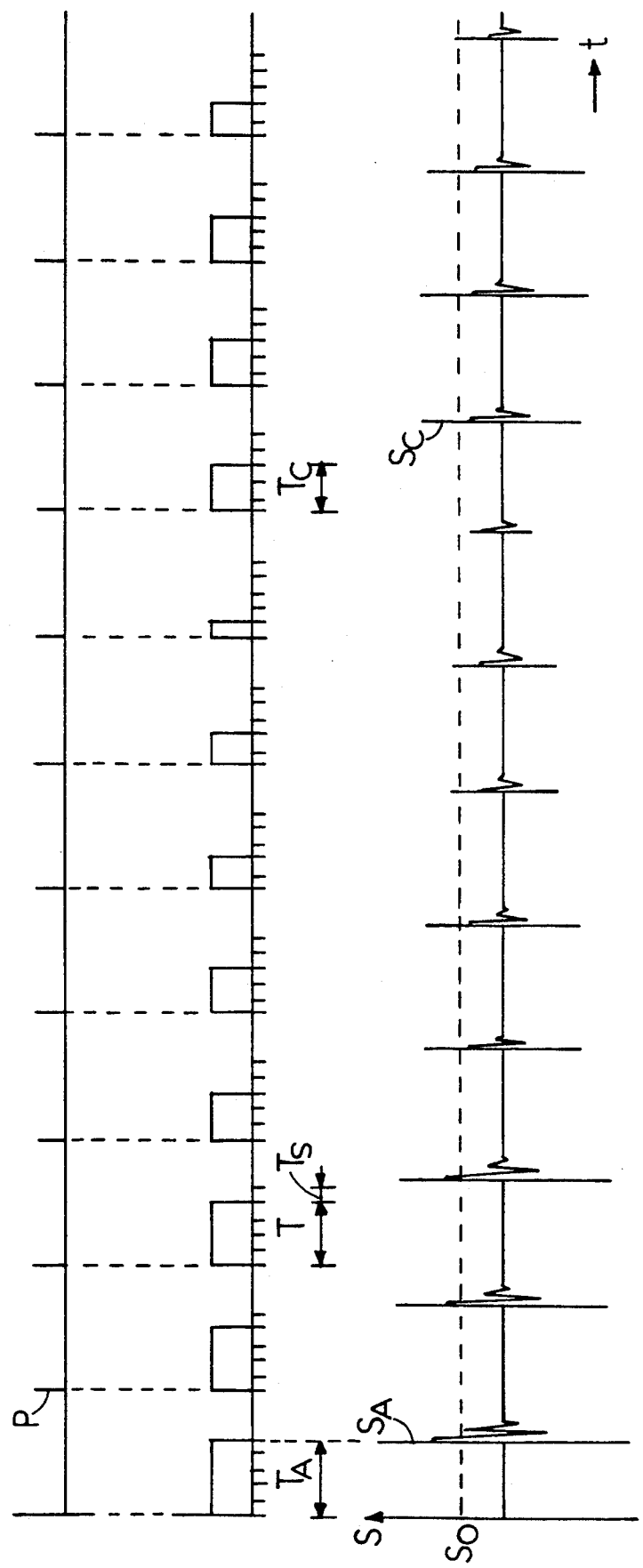
FIG. 4 shows the basic course over time of the variation of the on-time duration in the calculation of the shortest value of the on-time duration required for a complete pump action.

In a further embodiment of the invention explained with reference to FIG. 4, the turn-on time interval T is variable. The beginning of each pump stroke is marked with individual pulses P generated by the pump rate generator 42. Proceeding from a value for the on-time duration T at which an output signal s of the noise sensor 17 which is sure to exceed the sensitivity threshold $s_o$ is obtained (i.e. with the value $T_A$, for example), the time interval T is shortened by a prescribed step width $T_s$ after a prescribed number of pump strokes (two pump stroked in the embodiment of FIG. 4). This procedure is repeated until the output signal s of the noise sensor 17 falls below the sensitivity threshold $s_o$. At that time, the time duration is lengthened to the value $T_c$ by at least one step width $T_s$ (FIG. 3) and the new value is retained for a given time, or for a number of pump strokes until a new value for the on-time duration is calculated again by step-by-step shortening of the on-time duration T. This procedure is also initiated when the output signal of the noise sensor 17 is suddenly absent. Due to changes in the pump 1, changes in the catheter system, or due to external conditions such as pressure or temperature, or due to changes in the liquid to be conveyed, the piston motion may change, so that different output signals of the noise sensor 17 are obtained even with an unaltered on-time duration T for the electromagnetic excitation. The drive of the piston pump 4 is automatically matched to altered pump conditions by the step-by-step shortening of the on-time duration, until the absence of an impact of the piston 4 against the detent 29, which results in the subsequent lengthening of the on-time duration by at least one step width. If the length of the on-time duration exceeds a prescribed maximum value, or falls below a prescribed minimum value, an error message is generated by the error detector 49.

Information by means of which malfunctions in the pump operation can be identified, and possibly impending malfunctions can be detected in advance, are obtained by storing the occurrence of a failure to detect the piston impact, together with the pump rate.

In addition to or instead of detection by a noise sensor 17, the impact of the piston 4 against the detent 29 may be detected by types of sensors, for example an optical sensor or a magnetic proximity switch.

Although modifications and changes may be suggested by those skilled in the art, it is the intention of the inventor to embody within the patent warranted hereon all changes and modifications as reasonably and properly come within the scope of his contribution to the art.

I claim as my invention:

1. A dosing device for use with a liquid-containing reservoir, for controlled delivery of liquid from said reservoir to a delivery site, said dosing device comprising:

a piston pump having a piston in a cylinder housing having a detent, said piston being movable in a stroke between a quiescent position and a position in contact with said detent;

electromagnetic actuation means for causing said piston to move toward said detent from said quiescent position;

detector means for generating a signal upon impact of said piston with said detent;

control means for supplying a turn-on signal and a turn-off signal to said electromagnetic actuation means; and evaluation means, connected to said control means and supplied with said signal from said detector means, for setting the length of an on-time duration following a turn-on signal and for instructing said control means to generate said turn-off signal after the expiration of said on-time duration by setting said on-time duration to a length shorter than the time required for said piston to move from said quiescent position to said detent given fault-free operation, and for lengthening said on-time duration in the absence of a signal from said detector means for a first predetermined number of strokes within a second predetermined number of strokes.

2. A dosing device as claimed in claim 1 wherein said evaluation means comprises means for setting said on-time duration to a length sufficient to accelerate said piston against said detent given fault-free operation and for, when lengthening said on-time duration, instructing said control means to generate said turn-off signal when said signal is generated by said detector means.

3. A dosing device as claimed in claim 1 wherein said evaluation means comprises means for lengthening said on-time duration a predetermined amount each time a signal from said detector means is absent following a turn-on signal.

4. A dosing device as claimed in claim 1 wherein said evaluation means comprises, for calculating a shortest on-time duration, means for shortening said on-time duration step-by-step in successive strokes proceeding from an on-time duration at which said signal from said detector means is obtained until reaching an on-time duration at which said signal from said detector means is absent and thereafter lengthening said on-time duration by a predetermined amount.

5. A dosing device as claimed in claim 4 wherein said evaluation means comprises means for repeating the calculating of the shortest on-time duration at uniform intervals for dynamically adapting said on-time duration to energy consumption of said piston pump.

6. A dosing device as claimed in claim 4 wherein said detector means has a sensitivity threshold and wherein said evaluation means comprises means for setting a step width, for said step-by-step shortening of said on-time duration, at a step width value which is lower than a difference between a first on-time duration in said successive strokes which causes said piston to contact said detent with an impact below said sensitivity threshold and an on-time duration causing said piston to contact said detent with an impact which upwardly transgresses said sensitivity threshold.

7. A dosing device as claimed in claim 1 further comprising error detector means for generating an error message if said on-time duration set by said evaluation means exceeds a prescribed maximum value or falls below a prescribed minimum value.

8. A dosing device as claimed in claim 1 for use with an external programming device, and said dosing device further comprising telemetry means for telemetrically communicating with said external programming device.

9. A dosing device as claimed in claim 8 further comprising error detector means for transmitting an error message signal via said telemetry means to said external programming device upon a length of said on-time duration as set by said evaluation means exceeding a prescribed maximum value or falling below a prescribed minimum value.

10. A dosing device as claimed in claim 1 further comprising a memory connected to said evaluation means in which a current value for said on-time duration is entered given the absence of a signal from said detector means.

11. A dosing device as claimed in claim 1 further comprising a memory in which each on-time duration set by said evaluation means is entered.

12. A dosing device as claimed in claim 11 further comprising means for entering a current value of a pump rate of said piston pump together with each of said on-time durations entered in said memory.

13. A dosing device as claimed in claim 11 further comprising means for entering a time in said memory at which said impact of said piston with said detent occurs for each stroke.

14. A dosing device as claimed in claim 11 further comprising means for entering a time in said memory following said turn-on signal at which said piston begins to accelerate.

15. A dosing device as claimed in claim 1 wherein said piston pump exhibits a plurality of pump parameters, and further comprising a memory for storing said pump parameters for each pump stroke, and wherein said evaluation means includes means for generating an error message in the event of a pump malfunction determined by evaluating said pump parameters and said on-time duration.

16. A dosing device as claimed in claim 15 for use with an external programming device, and further comprising means for telemetrically communicating said error message to said external programming device.

17. A method for operating a dosing device for controlling delivery of a liquid through said dosing device from a reservoir to a delivery site, said method comprising the steps of:

moving a piston in a cylinder housing in a piston pump through a stroke between a quiescent position and a position in contact with a detent in said cylinder housing by electromagnetic actuation caused by excitation of an electromagnetic element starting with a turn-on signal and ending with a turn-off signal;

generating a signal by a detector means upon impact of said piston with said detent;

setting the length of an on-time duration following a turn-on signal to a length shorter than a time required for said piston to move from said quiescent position to said detent given fault-free operation and generating said turn-off signal upon the expiration of said on-time duration; and lengthening said on-time duration in the absence of a signal from said detector means for a first predetermined number of strokes within a second predetermined number of strokes.

18. A method as claimed in claim 17 wherein the step of setting said on-time duration is further defined by setting said on-time duration to a length sufficient for accelerating said piston against said detent given fault-free operation; and wherein the step of lengthening said on-time duration is further defined by generating said turn-off signal upon the generation of said signal indicating impact of said piston with said detent.

19. A method as claimed in claim 17 wherein in the step of lengthening said on-time duration is further defined by lengthening said on-time duration by a predetermined amount each time a signal indicating impact of said piston with said detent is absent following a turn-on signal.

20. A method as claimed in claim 17 comprising the additional step of calculating a shortest on-time duration by shortening said on-time duration step-by-step in successive strokes proceeding from an on-time duration which causes a signal indicating impact of said piston with said detent until reaching an on-time duration at which said signal indicating impact of said piston with said detent is absent, and thereafter lengthening said on-time duration by a predetermined amount.

21. A method as claimed in claim 20 comprising the additional sleep of repeating said calculation of the shortest on-time duration at uniform intervals for dynamically adapting said on-time duration to energy consumption of said piston pump.

22. A method as claimed in claim 20 wherein the step of generating a signal upon impact of said piston with said detent is further defined by detecting impact of said piston against said detent with a prescribed sensitivity threshold and generating said signal upon said impact exceeding said sensitivity threshold, and wherein the step of shortening said on-time duration step-by-step is further defined by setting a step width for shortening said on-time duration at a step width value which is less than the difference between a first on-time duration in said successive strokes for which said signal indicating impact of said piston with said detent is absent and an on-time duration at which said signal indicating impact of said piston with said detent is generated.

* * * * *